(12) United States Patent
Frank

(10) Patent No.: US 9,226,944 B2
(45) Date of Patent: Jan. 5, 2016

(54) HERBAL PREPARATION FOR SLEEP APNEA RELIEF

(76) Inventor: Steven R. Frank, Niwot, CO (US)

( * ) Notice: Subject to any disclaimer, the term of this patent is extended or adjusted under 35 U.S.C. 154(b) by 782 days.

(21) Appl. No.: 12/506,166

(22) Filed: Jul. 20, 2009

(65) Prior Publication Data
US 2010/0015261 A1 Jan. 21, 2010

Related U.S. Application Data

(60) Provisional application No. 61/135,362, filed on Jul. 21, 2008.

(51) Int. Cl.
| | | |
|---|---|---|
| *A61K 36/34* | (2006.01) | |
| *A61K 36/28* | (2006.01) | |
| *A61K 36/53* | (2006.01) | |
| *A61K 36/73* | (2006.01) | |
| *A61K 36/185* | (2006.01) | |

(52) U.S. Cl.
CPC ........... *A61K 36/28* (2013.01); *A61K 36/185* (2013.01); *A61K 36/34* (2013.01); *A61K 36/53* (2013.01); *A61K 36/73* (2013.01)

(58) Field of Classification Search
CPC ....... A61K 36/34; A61K 36/28; A61K 36/53; A61K 36/73
USPC ......... 424/765, 745, 764, 773, 774, 775, 778, 424/779
See application file for complete search history.

(56) References Cited

U.S. PATENT DOCUMENTS 4,855,143 A * 8/1989 Lowey .................. 424/468
5,403,595 A * 4/1995 Kitchell et al. ............... 424/501

OTHER PUBLICATIONS

Khare. Indian Herbal Remedies: Rational Western Therapy, Ayurvedic and Other Traditional Usage, Botany. Springer 2004. p. 292.*
Kenner et al. Botanical Medicine: A Eurpoean Professional Perspective. Paradigm Publications, 2001. p. 121.*
Matthew. Chamomile-Medicinal Uses, Interactions, Dosage. Ezine Articles. Feb. 8, 2007.*
Herbs2000.com. Crampbark. Retrieved from the internet. <http://replay.web.archive.org/20030518213419/http://www.herbs2000.com/herbs/herbs_crampbark.htm>. Retrieved on Apr. 28, 2011. Web archive date May 18, 2003. pp. 1-3.*
Ritchason. The Little Herb Encyclopedia. Woodland Publishing. 1995. p. 313.*

* cited by examiner

*Primary Examiner* — Chris R Tate
*Assistant Examiner* — Deborah Davis
(74) *Attorney, Agent, or Firm* — Lathrop & Gage LLP

(57) ABSTRACT

An herbal preparation for relief of sleep apnea contains lobelia and/or lobelia extract material acting as a respiratory stimulant in combination with meadowsweet to reduce nausea. Optional but preferred materials also include thyme to increase pleural activity, together with chamomile and cramp bark to facilitate relaxation.

16 Claims, No Drawings

HERBAL PREPARATION FOR SLEEP APNEA RELIEF

RELATED APPLICATIONS

This application claims benefit of priority to U.S. Provisional Application No. 61/135,362 filed Jul. 21, 2008.

BACKGROUND

1. Field

The present invention pertains to the field of herbal compositions. More particularly, the herbal composition may be used for relief of sleeping disorders, especially sleep apnea.

2. Description of the Related Art

Sleep apnea is one of the most common sleep disturbance problems in America. It ruins the sleep of an estimated 25 million Americans on a regular basis. The condition prevents the sleeper from entering rapid eye movement (REM or dream sleep) and Delta sleep modes. This causes the sufferer to become anxious, cantankerous and tired during the day. Serious health conditions are associated with prolonged sleep deprivation caused by sleep apnea. In one aspect, sleep apnea lowers blood oxygen levels below normal values for prolonged periods of time. This lack of oxygen has potential to damage to the brain and heart.

Despite the large number of people who suffer from sleep apnea, current treatment options are quite limited. Initially, the patient is told to loose weight, drink less alcohol and quit smoking; however, many patients are unwilling or unable to do those things. Surgery is offered to remove obstructions from the inhalation pathway. While the surgery option provides some limited successes, the procedure is painful and often provides no relief. The last option is for the patient to purchase a continuous positive airway pressure (CPAP) device. This is a forced air mask, worn during sleep, that insures proper inhalation. Most patients are unwilling to stand this expense, nor do they very well tolerate use of machinery that assists breathing in this manner.

None of these 'solutions' address the actual cause of the problem. Being over-weight does not cause sleep apnea. Smoking is not a cause, nor is sleeping on one's back. Sleep apnea results from competing regulatory control mechanisms of the body being out of balance.

Human bodies have numerous types and styles of control systems. Some systems regulate and maintain physiological conditions. For example, people who are in good health generally maintain core body temperature within a degree or so. The temperature control system always operates on an involuntary basis. The body regulates metabolism, smoothly and continuously providing just enough heat from digestion of food and stored fat to maintain the desired temperature. When body temperature rises too high, people begin proportionately releasing sweat to cool the body. When the temperature falls too low, people burn more stored fat to release energy. This illustrates of a proportional control system, i.e., one that makes continuous corrective actions in proportion to the error that the system is experiencing. Respiration is also a proportional system. As blood oxygen level starts to drop, respirations become deeper and more regular while the heart pumps faster.

Other types of control systems exist, and are known generally as bi-valent systems. These systems have one of two states: (1) active or (2) in-active. A good example of the bi-valent system is the gag reflex. When a foreign object advances down the throat, the body will convulsively expel the object by a rapid contraction of esophagus and stomach. This response is not proportional to the amount of penetration of the foreign object, nor is it proportional to the size of the object. It is an 'all or nothing' response. In a related example, one is ether vomiting or not vomiting.

Human bodies have many control systems, and many protective systems as well. Two systems affecting sleep apnea concern the respiration system. One system is proportional and the other system is bi-valent. As above, a control system is responsible for maintaining the blood oxygenation level. This is a proportional control system that controls the diaphragmatic muscles, in order to regulate the depth of respiration.

People fall asleep, and so also move through the various stages of sleep. Stage one is drowsiness. Stage two sleep is a transition stage before entering REM sleep. REM sleep is where we dream, which is essential to a good nights sleep. Muscular activity is inhibited in Stage 2, and this is commonly referred to as reduction of muscle tonus. This may be explained as a way to prevent the dreamer from physically acting out the movements of his or her heir dreams. This muscular inhibition becomes necessary because the part of the brain that controls muscular movement cannot tell the difference between a person who is dreaming about walking down stairs and one who is actually walking down stairs. The inhibition suppresses the movement of signals from the brain along the spinal cord. Some problems with the inhibition mechanism develop, especially as people age.

One problem is that the muscles of the soft palate in the back of the mouth become weaker, allowing the soft palate to sag. This is not particularly unusual, since most people are not professional vocalists and don't exercise their soft palate. As people age and levels of human growth hormone (HGH) drop, many muscles in the body atrophy to a lower level of capability.

Another problem is that the neuronal communication between the diaphragm and the brain becomes somewhat obstructed. The nerves that reach the diaphragm emanate from the spinal column at C3, C4 and C5. These cervical vertebrate are located at the insertion point of the upper trapezius muscles. The upper trapezius muscles may be significantly affected by stress to produce tension. This tension reduces the intervertebral foramen from which the nerves emanate, restricting the nervous flow along the root of the nerve through direct restriction. Significantly, a large amount of this tension is residual and does not dissipate when the subject enters stage two sleep.

The result of this is that upon entering stage two sleep the muscle tonus holding the soft palate out of the air-way is further reduced, allowing the soft palate to sag into the airway. While this is happening, the same inhibition of muscle tonus is further attenuating or reducing the neuronal signals to the diaphragm on the already obstructed nerves. Breathing becomes shallower and shallower due to the insufficient signal strength being delivered to the diaphragmatic muscles.

The blood oxygen level drops as breathing becomes shallower. In a young and healthy individual, this usually illicits stronger and deeper breathing from the proportional control system that regulates these activities. In some older individuals with restricted nervous flow to the diaphragmatic muscles, there is no residual ability to increase deeper breathing, due to the inhibition caused by stage two sleep entry and restricted nervous flow. The respirations reduce in intensity and, consequently, the blood oxygenation drops.

In sleep apnea. the normal proportional control loop is un-able to maintain the desired level of blood oxygenation. This is where the bi-valent safety back-up system comes into effect. When the blood oxygen level gets low enough to cause the individual to suffer physiological damage, the bi-valent system intervenes and causes the body to make a large and immediate inhalation. This causes a large pressure differential in the pharynx and literally sucks the sagging-soft palate into the airway. This obstructs the flow and causes a loud "SNORT," which awakens the subject.

Upon awakening, the inhibition causing the reduction of muscle tonus for entry into stage two sleep is released. Respiration begins again in a somewhat normal manner. As the subject starts to drift off to sleep again, he or she moves into Stage two. The muscle tonus drops, the soft palate sags, the signal to the diaphragm diminish and the cycle repeats. The resulting snorting awakenings typically occur every minute or so.

Problematically, the present modalities of treating sleep apnea do nothing to affect these regulatory and protective mechanisms.

SUMMARY

The present instrumentalities mitigate the problems outlined above and advance the art by providing an herbal preparation for sleep apnea relief. Without being bound by theory, the preparation appears to accentuate the ability of the brain to communicate with the diaphragm to maintain the proper blood oxygen levels and so also prevent the safety bi-valent system from causing a rapid inhalation that causes a person to awake. This is achieved by the administration of a few common herbs.

Small doses of Lobelia act as a respiratory stimulant. In larger doses, Lobelia has the opposite effect of decreasing respiration. This herb, when taken before bed in the proper dose, can increase the quiescent level of respiration sufficiently so as to avert the dangerous drop in blood oxygen level that occurs upon muscular inhibition. Even so, Lobelia is sometimes called "Puke weed" by Native Americans, and herbalists have a longstanding debate about the relative toxicity of Lobelia and various Lobelia extracts. Lobelia has unsettling effects on the stomach, so it is not commonly used. Effective doses of Lobelia for use as a respiratory stimulant range from 300 to 600 mg of the dried herb or equivalent constituent quantities extracted from this amount of herb. These dosages assume an average adult weighing from 100 to 170 pounds, as do the dosages provided below. Larger adults may require additional dosages, such as a second capsule with the recommended dosages. Adults in this weight range suffering from severe sleep apnea may also benefit from taking increased dosages, such as a second capsule.

In one aspect, Lobelia may be used in conjunction with another herb, such as meadowsweet, to eliminate nausea caused by Lobelia alone. Meadowsweet contains salicylates and is also an anti-inflammatory agent. This is further useful in that airway inflammation from allergens such as dust and pollen and low-level infections, otherwise, increase obstruction and aggravate sleep apnea. Reducing nasal inflammation is important in maintaining a clear airway for smooth breathing. Effective doses of meadowsweet for these purposes range from 50 to 200 mg of the dried herb or equivalent constituent quantities extracted from this amount of herb. Other stomach soothing agents that supplement the functionality of meadowsweet or may be used in place of meadowsweet include peppermint and ginger. Herbs in the class of carminative, antispasmodic or stomachic herbs are useful in this aspect.

Thyme is traditionally used to enhance pleural activity, and contributes to maintaining respiratory amplitude. Thyme for these purposes range from 20 to 500 mg of the dried herb or equivalent constituent quantities extracted from this amount of herb.

Relaxants may round out the combination. In one aspect, chamomile may be used as a sleep-aid relaxant. Chamomile is preferably but optionally included in an amount ranging from 20 to 200 mg of the dried herb or equivalent constituent quantities extracted from this amount of herb, aids the subject in relaxing. The chamomile helps subject relax in a manner such that they can drift off to sleep, and so is in the class of sedative or relaxant herbs. Others herbs of this nature that may be used in place of or in combination with chamomile include, for example, kava-kava, California poppy and passion flower.

In one aspect, cramp bark is a skeletal muscle relaxant. In particular, cramp bark helps the upper trapezius muscles to relax, and is preferably but optionally present in an amount ranging from 30 to 200 mg of the dried herb or equivalent constituent quantities extracted from this amount of herb. Additional herbs in the classes of antispasmodic, relaxant, or analgesic herbs are useful in this respect, and may include, for example, Mexican wild yam, arnica, and lavender.

This bouquet of herbs relaxes muscles that restrict nervous flow, increases drowsiness, enhances respiration and protects the stomach lining. It represents a holistic natural solution to sleep apnea. It is non-habit forming and no-preconditioning is required. The first night of an apnea episode will be mitigated within 30 to 60 minutes of ingesting a capsule. Bringing these herbs together in this way represents a completely new manner of treating sleep apnea. It addresses the cause with a therapeutic means.

One of the problems of ingesting herbs is the fact that it takes a while for the capsule to dissolve. It takes longer still to digest the herbs to a point where the desired constituents are adsorbed to appear in the blood stream. In the case of the previously described product, it can take from 30 to 60 minutes. This process can be accelerated in a number of ways.

In one aspect, the herbal preparation may be preprocessed by a simple extraction process of the vital constituents using water, steam, or another extraction agent. This produces a decoction or tincture that may be taken orally, inhaled or applied to the skin for absorption. Use of the decoction reduces the time that beneficial materials require to appear in the blood stream.

In one aspect, the herbal capsules tend to be effective for only about 6 hours. Thus, the sufferer wakes in the night needing another dose. This can be mitigated by taking two tablets or capsules of different release rates or a combined capsule/tablet with multiple release rates. One portion may be provided with thin wall of gelatin, starch, cellulose, and/or water-soluble polymer for absorption in the stomach. Another portion may be entero-coated to dissolve in the intestinal tract. This delayed second dose remediates a problem that the herbs of a single capsule tend to only work for six hours, whereas most people need at least about eight hours of sleep. Methods of formulating time release compositions are well known, for example, as taught in U.S. Pat. No. 5,702,723 "Multi-stage delivery system for ingestible medications or nutrients", and U.S. Pat. No. 4,855,143 "Method of preparing controlled long-acting pharmaceutical formulations in unit dosage form having uniform and comparable bioavailability characteristics, " each of which are hereby incorporated by reference to the same extent as though fully replicated herein.

Another aspect recognizes that lobeline is the active agent in the lobelia providing the respiratory stimulant functional ity. The other herbs are also functional. The lobeline may be combined with the other herbs or their extracted valuable constituents in a compounded manner. Lobeline may be extracted from lobelia and derivated to provide various useful forms. Thus, it is appropriate to use extracted forms of lobelia including lobeline, lobelanine, lobelanidine or lobeline sulfate or lobeline-hcl. As used herein, unless otherwise indicated to the contrary, the term "extracted forms of lobelia" includes also synthetic forms of these materials which may be either extracted or synthesized. Lobeline materials are commercially available nicotinic antagonists, and have been used for years to aid in smoking cessation programs. Dosages providing lobeline or derivated lobeline in the 1 to 5 mg range would be sufficient. Lobeline is also known as 2-[6-(2-hydroxy-2-phenyl-ethyl)-1-methyl-2-piperidyl]-1-phenyl-ethanone, and has a CAS Number 90-69-7. Lobeline hydrochloride may be purchased on commercial order from Acros Organics N.V. of Fair Lawn, N.J. and is also known as 2-[(6-β-hydroxyphenylethyl)-1-methyl-2-piperidyl]-acetophenone hydrochloride, having a CAS Number 63990-84-1. Lobeline sulfate may be purchased on commercial order from ScienceLab.com of Houston, Tex. and is also known as 2-[(6-hydroxy-2-phenylethyl)-1-methyl-2-piperidinyl]-phenylethanone sulfate, having a CAS Number 134-64-5.

In one aspect, using lobeline extracts or derivatives and compounds to treat sleep apnea in a liquid, gel, capsule or tablet form is an effective means for treating the problem without necessarily using raw herbs. Use of extracted materials tends to be more accepted in the medical community, since the exact doses of active agents may be controlled more readily.

Additionally, with the extraction and refining process, the constituents of Lobelia that are responsible for depressing the respiration can be removed so that higher doses are more effective. Also, the constituents that are responsible for the nausea can be removed so as to allow higher doses to be tolerated more easily and comfortably.

Lobelia contains about 0.24-0.48% piperidine alkaloids, of which lobeline is considered the major component. Lobelia contains other less-known alkaloids, such as lobelanine, lobelanidine, norlobelanine, lelobanidine, norlelobanidine, norlobelanidine, and lobinine, Newall, Carol A., Linda A. Anderson and J. D. Phillipson., *Herbal Medicines: A Guide for Health-Care Professionals*. London: The Pharmaceutical Press p. 187 (1996); Evans, W. C., *Trease and Evans Pharmacognosy* London: BailliEre Tindall p. 575 (1989) Other constituents include a bitter glycoside called lobelacrin, chelidonic acid, fats, gum, resin and volatile oil. Lobeline is stable when combined with the plant, but decomposes when freed from contact with the other constituents of the plant. Heat accelerates this decomposition.

As stated above, small doses of Lobelia increase respiration, whereas larger doses decrease respiration. This effect of decreasing respiration at larger doses may be mitigated by removing other alkaloids from the preparation. Nausea may be similarly mitigated. Lobeline is traditionally obtained from Lobelia by depriving Lobelia seeds of fat by means of benzine, abstracting the seeds with alcohol acidulated with acetic acid in a percolator, and evaporating and extracting the alkaloid with ammoniated ether. Chromatography may also be used. Increasingly purified forms of Lobelia, or synthetic forms of lobeline and homologues thereof, are advantageously associated with less nausea and less decrease of respiration.

DETAILED DESCRIPTION

The following instrumentalities teach by way of example and not by limitation. Thus, the examples should not be construed as unduly limiting what is claimed as the invention.

EXAMPLE 1

Herbal Preparation for Relief of Sleep Apnea

| Ingredient | Weight, mg |
| --- | --- |
| Lobelia | 400 |
| Meadowsweet | 100 |
| Thyme | 50 |
| Chamomile | 50 |
| Cramp Bark | 50 |
| Total | 650 |

The formulation of Table 1 was prepared as the contents of a gelatin capsule.

EXAMPLE 2

Use of Herbal Preparation

One capsule of the herbal preparation from Example 1 is administered to a human test subject diagnosed as having sleep apnea. The capsule is administered 30 minutes before bed-time. Doses are limited to no more than two capsules in one night. The human test subject experiences a more restful sleep undisturbed by the effects of sleep apnea. There are fewer cessations of breathing and the breathing intensity is deeper and more even.

Those skilled in the art appreciate that small differences may be made to what is taught above, without departing from the scope and spirit of the invention. Accordingly, the inventor states his intention to rely upon the Doctrine of Equivalents to protect the full scope of what is claimed.

I claim:

1. A dosage preparation for relieving sleep apnea, comprising:
   300 mg to 600 mg of Lobelia and/or an extract thereof;
   50 mg to 200 mg of meadowsweet and/or an extract thereof;
   20 mg to 500 mg of thyme and/or an extract thereof;
   20 mg to 200 mg of chamomile and/or an extract thereof; and
   30 mg to 200 mg of cramp bark and/or an extract thereof.

2. The preparation of claim 1, wherein the Lobelia and/or extract thereof acts as a respiratory stimulant and is present in an amount of about 400 mg.

3. The preparation of claim 1, wherein the meadowsweet and/or extract thereof acts as a stomach soothing agent to reduce nausea caused by the Lobelia or extract thereof.

4. The preparation of claim 1, wherein the chamomile and/or extract thereof acts as an herbal sleep aid relaxant to assist a subject in going to sleep.

5. The preparation of claim 1, wherein the cramp bark and/or extract thereof acts as an herbal skeletal muscle relaxant to assist a subject in relaxation of skeletal muscles.

6. The preparation of claim 1, further comprising an agent for delaying adsorption of the Lobelia and/or extract thereof and the meadowsweet and/or extract thereof after oral consumption of the preparation by a human subject.

7. The preparation of claim 2, wherein the Lobelia or extract thereof is essentially free of extraneous alkaloids, other than Lobeline,
that induce nausea or decrease respiration.

8. A dosage preparation for relieving sleep apnea, comprising:
- 1 mg to 5 of a compound selected from the group consisting of lobeline, lobelanine, lobelanidine, lobeline sulfate, lobeline hydrochloride, and mixtures thereof;
- 50 mg to 200 mg of meadowsweet and/or an extract thereof;
- 20 mg to 500 mg of thyme and/or an extract thereof;
- 20 mg to 200 mg of chamomile and/or an extract thereof; and
- 30 mg to 200 mg of cramp bark and/or an extract thereof.

9. The preparation of claim 8, wherein the meadowsweet and/or extract thereof acts as a stomach soothing agent to reduce nausea caused by the Lobelia or extract thereof.

10. The preparation of claim 8, wherein the chamomile and/or extract thereof acts as an herbal sleep aid relaxant to assist a subject in going to sleep.

11. The preparation of claim 8, wherein the cramp bark and/or extract thereof acts as an herbal skeletal muscle relaxant to assist a subject in relaxation of skeletal muscles.

12. The preparation of claim 8, further comprising an agent for delaying adsorption of the Lobelia and/or extract thereof and the meadowsweet and/or extract thereof after oral consumption of the preparation by a human subject.

13. The preparation of claim 1, wherein the preparation is in the form of a capsule.

14. The preparation of claim 8, wherein the preparation is in the form of a capsule.

15. A method of treating sleep apnea in a subject, comprising:
identifying a subject who suffers from sleep apnea, and
administering the dosage preparation of claim 1 to said subject.

16. A method of treating sleep apnea in a subject, comprising:
identifying a subject who suffers from sleep apnea, and
administering the dosage preparation of claim 8 to said subject.

* * * * *